United States Patent [19]

Chou et al.

[11] Patent Number: 5,019,663
[45] Date of Patent: May 28, 1991

[54] HEAT BALANCED PARAFFIN UPGRADING WITH CO-FED OXYGENATE

[75] Inventors: Tai-Sheng Chou, Pennington; Melcon G. Melconian, Princeton, both of N.J.

[73] Assignee: Mobil Oil Corp., Fairfax, Va.

[21] Appl. No.: 332,185

[22] Filed: Apr. 3, 1989

[51] Int. Cl.$^5$ .............................................. C07C 15/00
[52] U.S. Cl. ................................... 585/415; 585/417; 585/640
[58] Field of Search ........................ 585/415, 417, 640

[56] References Cited

U.S. PATENT DOCUMENTS

| | | | |
|---|---|---|---|
| 3,136,713 | 6/1964 | Miale et al. | 208/113 |
| 3,254,023 | 5/1966 | Miale et al. | 208/120 |
| 3,267,023 | 8/1966 | Miale et al. | 208/111 |
| 3,760,024 | 9/1973 | Cattanach | 260/673 |
| 3,845,150 | 10/1974 | Yan et al. | 260/673.5 |
| 3,931,349 | 1/1976 | Kuo | 260/668 R |
| 3,960,978 | 6/1976 | Givens et al. | 260/683.15 |
| 3,998,899 | 12/1976 | Daviduk et al. | 260/668 R |
| 4,021,502 | 5/1977 | Plank et al. | 260/683.15 |
| 4,035,430 | 7/1977 | Dwyer et al. | 260/668 R |
| 4,150,062 | 5/1979 | Garwood et al. | 260/673 |
| 4,211,640 | 7/1980 | Garwood et al. | 208/255 |
| 4,227,992 | 10/1980 | Garwood et al. | 208/46 |
| 4,404,414 | 9/1983 | Penick et al. | 585/469 |
| 4,550,217 | 10/1985 | Graziani et al. | 585/640 |
| 4,720,602 | 1/1988 | Chu | 585/417 |

OTHER PUBLICATIONS

"Cyclar: One Step Processing of LGP to Aromatics and Hydrogen", R. F. Anderson, J. A. Johnson and J. R. Mowry.

Primary Examiner—Curtis R. Davis
Attorney, Agent, or Firm—Alexander J. McKillop; Charles J. Speciale; Robert B. Furr, Jr.

[57] ABSTRACT

The endothermic heat of reaction for zeolite-catalyzed paraffin aromatization is provided by a co-fed oxygenate stream. Advantageously, the addition of a dehydrogenation metal to the zeolite reduces the reaction temperature for paraffin aromatization to a range suitable for the exothermic conversion of an oxygenate to $C_5+$ gasoline. Preferred paraffinic feedstreams include $C_3$-$C_4$ LGP and the preferred oxygenate is methanol.

20 Claims, No Drawings

HEAT BALANCED PARAFFIN UPGRADING WITH CO-FED OXYGENATE

FIELD OF THE INVENTION

The present invention relates to the conversion of relatively low value light paraffinic streams to more valuable olefinic and aromatic streams. More in particular, the invention relates to a process for the aromatization of $C_2$-$C_4$ predominately paraffinic streams in which at least a portion of the endothermic heat of reaction is supplied by the exothermic conversion of oxygenates such as methanol.

BACKGROUND OF THE INVENTION

Developments in zeolite catalysts and hydrocarbon conversion processes have created interest in utilizing light aliphatic feedstocks for producing $C_5+$ gasoline, diesel fuel, etc. In addition to basic chemical reactions promoted by medium-pore zeolite catalysts, a number of discoveries have contributed to the development of new industrial processes. These are safe, environmentally acceptable processes for utilizing feedstocks that contain olefins. Conversions of $C_2$-$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al have also contributed to the understanding of catalytic olefin upgrading techniques and improved processes as in U.S. Pat. Nos. 4,150,062, 4,211,640 and 4,227,992. The above-identified disclosures are incorporated herein by reference.

Catalytic aromatization of light paraffinic streams, e.g. $C_2$-$C_4$ paraffins, commonly referred to as LPG, is strongly endothermic and typically carried out at temperatures between 540° and 820° C. (1000° and 1500° F.). While the incorporation of hydrogenation/dehydrogenation metals including gallium, platinum, indium, tin and mixtures thereof in zeolite catalysts may reduce the operating temperature to the range of about 400° to 600° C. (750° to 1100° F.), the problem of transferring sufficient heat to a catalytic reaction zone to carry out the paraffin upgrading reaction remains as an obstacle to commercialization of the process.

Methods of supplying heat to the endothermic reaction zone include indirect heat exchange, e.g. a multi-bed reactor with inter-bed heating. Direct heat exchange techniques include oxidative dehydrogenation of a portion of the feedstream. Unfortunately, however, oxidative dehydrogenation is accompanied by a loss of a valuable by-product, hydrogen. Further, the incremental costs associated with maintaining a controlled supply of a suitable oxygen source, e.g. $NO_x$, $CO_2$ or $SO_3$, makes commercialization of such schemes impractical. Clearly, for the coupling of an exothermic reaction with the endothermic paraffin upgrading process to be economically beneficial, the exothermic reaction must not defeat the economic viability of the primary conversion reaction.

Processes for converting lower oxygenates such as methanol and dimethyl ether to hydrocarbons are known and have become of great interest in recent times because they offer an attractive way of producing liquid hydrocarbon fuels, especially gasoline, from sources which are not of liquid petroliferous origin. In particular, they provide a way by which methanol can be converted to gasoline boiling range products in good yields. The methanol, in turn, may be readily obtained from coal by gasification, to synthesis gas and conversion of the synthesis gas to methanol by well-established industrial processes. As an alternative, the methanol may be obtained from natural gas by other conventional processes.

The conversion of methanol and other lower aliphatic oxygenates to hydrocarbon products may take place in a fixed bed process as described in U.S. Pat. Nos. 3,998,899; 3,931,349 (Kuo) and 4,035,430. In the fixed bed process, the methanol is usually first subjected to a dehydrating step, using a catalyst such as gamma-alumina, to form an equilibrium mixture of methanol, dimethyl ether (DME) and water. This mixture is then passed at elevated temperature and pressure over a catalyst such as ZSM-5 zeolite for conversion to the hydrocarbon products which are mainly in the range of light gas to gasoline. Water may be removed from the methanol dehydration products prior to further conversion to hydrocarbons and the methanol can be recycled to the dehydration step, as described in U.S. Pat. No. 4,035,430. Removal of the water is desirable because the catalyst may tend to become deactivated by the presence of excess water vapor at the reaction temperatures employed; but this step is not essential.

Thermal balance is a major problem in the operation of an adiabatic process. Process development involving exothermic reactions, e.g. conversion of methanol to hydrocarbons over a zeolite-containing catalyst, clearly demonstrates the significant impact of the problem of dissipating excess thermal energy as well as the costs for heat removal equipment.

The conversion of the oxygenated feed stream (methanol, DME) to the hydrocarbons is a strongly exothermic reaction liberating approximately 1480 kJ. (1400 Btu) of heat per kilogram of methanol. In an uncontrolled adiabatic reactor this would result in a temperature rise which would lead to extremely fast catalyst aging rates or even to damage to the catalyst. Furthermore, the high temperatures which might occur could cause undesirable products to be produced or the product distribution could be unfavorably changed. It is therefore necessary that some method should be provided to maintain the catalyst bed within desired temperature limits by dissipating the heat of the reaction.

One method is to employ a light gas portion of the hydrocarbon products as recycle, as desccibed in U.S. Pat. No. 3,931,349 (Kuo). Typically, cooled light hydrocarbon gas, rich in methane, ethane, etc., is separated from the gasoline and LPG products, re-compressed and reheated before being mixed with the reactant feedstream entering the bed of conversion catalyst. Although effective in controlling bed temperature, the expense of cooling the recycle gas, compressing it and re-heating it add to the cost of the conversion, indicating that a reduction in recycle ratio would be economically desirable. The recycle ratio can indeed be decreased but only with certain disadvantages. Not only will the temperature rise across the catalyst bed be greater, thereby increasing the aging rate of the catalyst but, in addition, the reactor must be operated at a lower and generally less favorable temperature; the outlet temperatures must be lowered in order to protect the catalyst from the increased partial pressure of the water which is consequent upon the lower partial pressure of the recycle gas and the inlet temperature must be lowered even further in order to compensate for the greater temperature rise across the catalyst bed. This is generally undesirable because the octane number of the gasoline product is related to reactor temperature with the higher octane products being produced at the higher temperatures. There is also a minimum reactor inlet temperature that must be maintained for the conversion to proceed and consequently, there is a limit on the extent to which the recycle ratio can be reduced.

A similar proposal is set out in U.S. Pat. No. 4,404,414. The process described in this patent employs a number of fixed bed reaction zones in which oxygenated feedstock is converted to hydrocarbon products by means of contact with a conversion catalyst. The temperature in the reactors is maintained at the desired value by the use of a diluent which is passed through the reactors in sequence before it is completely cooled and separated from the conversion products. The diluent in this case is light hydrocarbon gases which have been separated from the liquid hydrocarbon products and water. Once again, the expense of cooling the recycle gas, compressing it and re-heating it add to the cost of the conversion.

A somewhat similar challenge involves supplying the required heat for processes involving highly endothermic reactions.

U.S. Pat. No. 3,136,713 to Miale et al teaches a method for heating a reaction zone by selectively burning a portion of a combustible feedstream in a reaction zone. Heat is directly transferred from the exothermic oxidation reaction to supply the endothermic heat for the desired conversion reaction.

Heat balanced reactions are also taught in U.S. Pat. Nos. 3,254,023 and 3,267,023 to Miale et al.

U.S. Pat. No. 3,845,150 to Yan and Zahner teaches a heat balanced process for the aromatization of hydrocarbon streams by combining the exothermic aromatization of light olefins with the endothermic aromatization of saturated hydrocarbons in the presence of a medium-pore zeolite catalyst.

U.S. Pat. No. 4,431,519 to La Pierre et al. teaches a process for the hydrodewaxing of distillate in which an organic oxygenate reacts exothermically in the dewaxing reaction zone to supply the endothermic heat of reaction for the catalytic dewaxing process.

Aromatization of $C_3$-$C_4$ paraffin-rich streams (commonly known as LPG), is highly endothermic. The aromatization reaction may be carried out in a fixed, moving or fluid catalyst bed. For example, the CYCLAR (tradename) process for LPG aromatization uses a plurality of moving-bed reaction zones together with continuous catalyst regeneration (CCR) to supply the required heat for the primary endothermic reaction. This commercial process scheme involving transporting hot catalyst pellets between the reaction and regeneration zones requires extensive capital investment.

The CYCLAR (tradename) process is described in the paper "CYCLAR: One Step Processing of LPG to Aromatics and Hydrogen," by R. F. Anderson, J. A. Johnson and J. R. Mowry presented at the AIChE Spring National Meeting, Houston, Tex., Mar. 24-28, 1985.

From the foregoing it can be seen that the combination of endothermic reactions with exothermic reactions for the purpose of heat balancing is desirable and can be particularly advantageous when both reactions act in concert to yield useful products. The combination of such reactions to provide a substantially heat balanced reaction zone would be still more beneficial if feedstreams having a relatively low economic value could be upgraded in such a heat balanced reaction zone to provide product streams having a substantially increased economic value.

The availability of liquified petroleum gas (LPG), specifically butane, is expected to increase in the near future. Butane is presently a valuable gasoline blending component which provides among other benefits, excellent winter cold-starting characteristics for automotive gasolines. Butane improves cold starting by readily volatilizing inside the engine cylinders. Unfortunately, butane's relatively high volatility raises the vapor pressure of the gasoline. Environmental concerns relating to evaporative gasoline losses to the atmosphere have prompted more stringent regulations requiring motor gasolines to be less volatile.

Rather than sell butane at lower valued LPG, it would be preferable to convert this stream to a high octane blending component having acceptable volatility (vapor pressure) characteristics. As mentioned above, it would be still more preferable to upgrade butane and other light $C_4$-paraffins while avoiding high capital and operating costs associated with strongly endothermic paraffin aromatization.

SUMMARY OF THE INVENTION

The present invention provides a process for catalytically upgrading a stream containing $C_2$-$C_4$ paraffins in which at least a portion of the endothermic heat of reaction required is supplied by the conversion of a cofed organic oxygenate stream. More specifically, the process of the present invention comprises the steps of maintaining a reaction zone containing a zeolite catalyst, charging the feedstream containing $C_2$-$C_4$ paraffins to the reaction zone under conversion conditions sufficient to convert at least a portion of the $C_2$-$C_4$ paraffins to aromatics and cofeeding to the reaction zone an organic oxygenate at a flowrate such that the exothermic reaction of the organic oxygenate provides at least a portion of the endothermic heat of reaction for the conversion of the $C_2$-$C_4$ paraffins.

DETAILED DESCRIPTION

Hydrocarbon feedstocks which can be converted according to the present process include various refinery streams including coker gasoline, light FCC gasoline, $C_5$-$C_7$ fractions of straight run naphthas and pyrolysis gasoline, as well as raffinates from a hydrocarbon mixture which has had aromatics removed by a solvent extraction treatment. Examples of such solvent extraction treatments are described in *Kirk-Othmer Encyclopedia of Chemical Technology*, Third Edition, Vol. 9, 706–709 (1980). A particular hydrocarbon feedstock derived from such a solvent extraction treatment is a Udex raffinate. Propane- and butane-rich refinery streams commonly referred to as LPG are particularly preferred for upgrading to aromatics and olefins in the process of the present invention.

The reaction severity conditions can be controlled to optimize yield of $C_6$-$C_8$ BTX (benzene, toluene and xylene) hydrocarbons. It is understood that aromatics and light olefin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 40 to significantly lower values. If the process is carried out in a fluid bed of catalyst, alpha value may be maintained by controlling fresh catalyst makeup as well as catalyst deactivation and regeneration rates to provide an apparent average alpha value (based on total catalyst inventory) below 40, e.g. about 20.

Process Conversion Conditions

The details of the catalytic aromatization of paraffinic feedstocks are set forth in the references cited above which are incorporated by reference as if set forth at length herein. Catalytic aromatization of light $C_4$-aliphatic streams is further described in the article, "M2 Forming-A Process for Aromatization of Light Hydrocarbons", by N. Y. Chen and T. Y. Yan, Ind. and Eng. Chem. Process Des. Dev., 151 (1986), which article is incorporated herein by reference. More specifically, the conversion conditions for the aromatization of light $C_4$-aliphatic streams are set forth in Table 1.

TABLE 1

| Upgrading Reaction Process Conditions | |
|---|---|
| WHSV | Broad range: 0.3–300 hr$^{-1}$ |
| | Preferred range: 0.5–10 hr$^{-1}$ |
| Operating Pressure | Broad: 170–2170 kPa (10–300 psig) |
| | Preferred: 170–790 kpa (10–100 psig) |
| Operating Temperature | Broad: 400–820°C. (750–1500° F.) |
| | Preferred: 400–600° C. (750–1100° F.) |

Exothermic Conversion of Organic Oxygenates

In addition to the references cited above in the Background section, the conversion of oxygenates such as methanol to gasoline is taught, for example, in U.S. Pat. Nos. 3,998,899 to Daviduk et al. and 3,931,349 to Kuo, as well as 4,035,430 to Dwyer et al., the disclosures of which are incorporated herein by reference.

In the process of the present invention, the endothermic heat of reaction required to aromatize the paraffinic feed is at least partially supplied by the exothermic conversion of oxygenates to gasoline. Preferred oxygenates include $C_4$-alcohols, and methanol is particularly preferred.

Methanol is not only a readily available and economical raw material, but is also more strongly exothermic than ethanol or propanol upon catalytic conversion to gasoline. For example, the amount of heat generated in the conversion of the lower alcohols to hydrocarbon mixtures that contain preponderant quantities of gasoline hydrocarbons may be estimated to be in the ranges shown:

| Alcohol Reactant | Heat Produced, BTU per lb. Hydrocarbons |
|---|---|
| Methanol | 1300–2000 |
| Ethanol | 280–620 |
| Propanol | 20–360 |

Advantageously, the process conditions for light paraffin aromatization overlap those for methanol conversion to gasoline. Further, both paraffin aromatization and conversion of methanol to gasoline are catalyzed by medium pore zeolites. It has been found that the addition of a dehydrogenation metal such as gallium to the zeolite lowers the paraffin aromatization temperature range to the preferred range between about 400° and 600° C. (750° and 1100° F.), enabling the endothermic aromatization reaction to proceed in the preferred temperature range for the exothermic conversion of methanol to gasoline. Useful reactor configurations include fixed, fluid and moving-bed designs.

Catalysts

The members of the class of zeolites useful in the process of the present invention have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as is set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. Nos. 4,350,835 and 4,686,312, both of which are incorporated by reference as if set forth in length herein.

Zinc-containing zeolite catalysts are also preferred for use in the present invention, for example, U.S. Pat. Nos. 4,392,989 and 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Dehydrogenation Components

Paraffin dehydrogenation components which may be added to the zeolite catalyst include oxides and sulfides of Groups IIIB, IVA, VA, VIA, VIIA and VIIIA and mixtures thereof. Thus, dehydrogenation may be promoted by sulfides and oxides of gallium, indium, titanium, zirconium, vanadium, mobium, tantalum, chromium, molybdenum, tungsten and mixtures thereof. Oxides of chromium alone or in conjunction with other catalytically active species have been shown to be particularly useful in dehydrogenation. Other catalytically active compounds include sulfides and oxides of manganese, iron, cobalt, rhodium, iridium, nickel, palladium, platinum and mixtures thereof.

The above-listed metals of Groups IIIB, IVA, VA, VIA, VIIA and VIIIA may be exchanged onto zeolites to provide a zeolite catalyst having dehydrogenation activity. Gallium has been found to be particularly useful for promoting dehydrogenation in the present process.

EXAMPLE

A typical refinery $C_3$–$C_4$ paraffinic stream (LPG) is upgraded to a $C_5+$ gasoline stream rich in aromatics in a heat balanced fluid bed reaction zone with controlled addition of methanol.

| LPG Composition, wt % | |
| --- | --- |
| $H_2$ | 0 |
| $C_1$ | 0 |
| $C_2$ | 3.9 |
| $C_2=$ | 0 |
| $C_3$ | 25.3 |
| $C_3=$ | 0.3 |
| $C_4$ | 68.8 |
| $C_4=$ | 0.7 |
| $C_5+$ | 1.0 |

The LPG and methanol feedstreams are preheated to a temperature of about 450° C. (850° F.) and charged to the fluid bed reaction zone. Combined feed rate is maintained at a level sufficient to provide a sub-transport fluid bed of catalyst. The relative flowrates of LPG and methanol are controlled via temperature/flowrate feedback controllers. The control circuit increases the relative flow of methanol upon sensing a decrease in reaction zone temperature. For the LPG feedstream composition listed above, heat balanced reaction zone operation is achieved at a weight ratio of about 1.3 kg methanol per 1 kg of LPG reactor charge.

Changes and modifications in the specifically described embodiments can be carried out without departing from the scope of the invention which is intended to be limited only by the scope of the appended claims.

What is claimed is:

1. A process for catalytically upgrading a feedstream containing $C_2$–$C_4$ paraffins comprising the steps of:
   (a) maintaining a metal-containing zeolite catalyst within a reaction zone;
   (b) charging said feedstream containing $C_2$–$C_4$ paraffins to said reaction zone under conversion conditions sufficient to convert at least a portion of said $C_2$–$C_4$ paraffins to aromatics; and
   (c) cofeeding to said reaction zone an organic oxygenate at a flowrate such that the exothermic reaction of said organic oxygenate provides at least a portion of the endothermic heat of reaction for the conversion of said $C_2$–$C_4$ paraffins.

2. The process of claim 1 further comprising maintaining the flowrate of organic oxygenate cofeed as recited in step (c) at a rate sufficient for substantially heat-balanced operation of said reaction zone.

3. The process of claim 1 wherein said organic oxygenate comprises at least one selected from the group consisting of methanol, ethanol, and their respective ethers.

4. The process of claim 3 wherein said organic oxygenate comprises methanol.

5. The process of claim 1 wherein said catalyst comprises a zeolite having a Constraint Index of between about 1 and about 12.

6. The process of claim 5 wherein said zeolite has the structure of at least one selected from the group consisting of ZSM-5, ZSM-11, ZSM-12, ZSM-22, ZSM-23, ZSM-35 and ZSM-48.

7. The process of claim 6 wherein said catalyst has the structure of ZSM-5.

8. The process of claim 6 wherein said zeolite contains at least one metal selected from Groups IIIB, IVA, VA, VIIA and VIIIA of the Periodic Table of the Elements.

9. The process of claim 7 wherein said zeolite contains at least one of the group consisting of Ga, Pt, In and Sn.

10. The process of claim 1 wherein said conversion conditions include pressures between 170 and 2170 kPa (10 and 300 psig), temperatures between 400° and 820° C. (750° and 1500° F.) and WHSV between 0.3 and 300 $hr^{-1}$.

11. The process of claim 1 wherein said conversion conditions include pressures between 170 and 790 kPa (10 and 100 psig), temperatures between 400° and 600° C. (750° and 1100° F.) and WHSV between 0.5 and 10 $hr^{-1}$.

12. The process of claim 11 further comprising maintaining said zeolite catalyst in a fixed bed.

13. The process of claim 11 further comprising maintaining said zeolite catalyst in a fluid bed.

14. A method for heat balancing a catalytic paraffin aromatization reaction zone to maintain said reaction zone at a desired conversion temperature between about 400° and about 820° C., said reaction zone containing a zeolite catalyst having a dehydrogenation metal component, said method comprising the steps of:
   (a) flowing a paraffinic feedstream and an oxygenate feedstream to said catalytic reaction zone under conversion conditions to convert at least a portion of said paraffinic feedstream to $C_5+$ aromatics and at least a portion of said oxygenate feedstream to $C_5+$ gasoline;

(b) measuring the temperature of said catalytic reaction zone;

(c) adjusting the relative flowrates of said oxygenate feedstream and said paraffinic feedstream to maintain a desired conversion temperature within said catalytic reaction zone by increasing the relative flowrate of said oxygenate feedstream if the measured catalytic reaction zone temperature of step (b) falls below said desired conversion temperature and decreasing the relative flowrate of said oxygenate feedstream if the measured catalytic reaction zone temperature of step (b) rises above said desired conversion temperature.

15. The method of claim 14 wherein said catalyst comprises a zeolite having a Constraint Index of between about 1 and about 12.

16. The process of claim 15 wherein said zeolite has the structure of at least one selected from the group consisting of ZSM-5, ZSM-11, ZSM-12, ZSM-22, ZSM-23, ZSM-35 and ZSM-48.

17. The process of claim 16 wherein said zeolite contains at least one of the group consisting of Ga, Pt, In and Sn.

18. The process of claim 14 wherein said catalytic reaction zone comprises a fluid bed of zeolite catalyst.

19. The process of claim 14 wherein said catalytic reaction zone comprises a fixed bed of zeolite catalyst.

20. A process for converting a feedstream containing $C_2$-$C_4$ paraffins to a product stream enriched in aromatics comprising the steps of:

(a) maintaining a metal-containing zeolite catalyst within a reaction zone;

(b) cofeeding said feedstream containing $C_2$-$C_4$ paraffins to said reaction zone with an organic oxygenate under conversion conditions sufficient to convert at least a portion of both said $C_2$-$C_4$ paraffins to aromatics and said organic oxygenate to gasoline boiling range hydrocarbons by controlling the relative flowrates of said feedstream containing $C_2$-$C_4$ paraffins such that the exothermic reaction of said organic oxygenate provides at least a portion of the endothermic heat of reaction for the conversion of said feedstream containing $C_2$-$C_4$ paraffins.

* * * * *